(12) United States Patent
Hoeppner

(10) Patent No.: US 10,893,857 B2
(45) Date of Patent: Jan. 19, 2021

(54) METHOD AND APPARATUS FOR COUPLING SOFT TISSUE TO BONE

(71) Applicant: Biomet Sports Medicine, LLC, Warsaw, IN (US)

(72) Inventor: Jacy C. Hoeppner, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 520 days.

(21) Appl. No.: 15/629,798

(22) Filed: Jun. 22, 2017

(65) Prior Publication Data

US 2017/0281153 A1 Oct. 5, 2017

Related U.S. Application Data

(63) Continuation of application No. 14/202,628, filed on Mar. 10, 2014, now Pat. No. 9,717,491.

(51) Int. Cl.
| | |
|---|---|
| *A61B 17/04* | (2006.01) |
| *A61B 17/17* | (2006.01) |
| *A61B 17/29* | (2006.01) |

(52) U.S. Cl.
CPC .......... *A61B 17/0401* (2013.01); *A61B 17/17* (2013.01); *A61B 2017/0406* (2013.01);
(Continued)

(58) Field of Classification Search
CPC ................ A61B 17/0401; A61B 17/17; A61B 2017/0406; A61B 2017/0409;
(Continued)

(56) References Cited

U.S. PATENT DOCUMENTS

| | | | | |
|---|---|---|---|---|
| 5,147,373 A | | 9/1992 | Ferzli | |
| 5,250,055 A | * | 10/1993 | Moore | ............... A61B 17/1796 606/148 |

(Continued)

FOREIGN PATENT DOCUMENTS

| | | |
|---|---|---|
| SU | 1600713 A1 | 10/1990 |
| WO | WO-9203980 A1 | 3/1992 |

(Continued)

OTHER PUBLICATIONS

"U.S. Appl. No. 14/202,628, Examiners Interview Summary dated Mar. 27, 2017", 1 pg.

(Continued)

*Primary Examiner* — Jing Rui Ou
(74) *Attorney, Agent, or Firm* — Schwegman Lundberg & Woessner, P.A.

(57) ABSTRACT

A method and apparatus for securing a suture to bone can include grasping a first suture portion with a grasping member on a positioning tool. The first suture portion can be located into a first cannulation defined in the positioning tool. A cutting member can be advanced through a second cannulation defined on the positioning tool and out through a distal opening defined on the positioning tool. A first bone hole can be cut into the bone with the cutting member. A flexible member advancing tool can be advanced through the first cannulation. The first suture portion can be urged out of the distal opening and into the first bone hole.

20 Claims, 6 Drawing Sheets

(52) U.S. Cl.
CPC ............... *A61B 2017/0409* (2013.01); *A61B 2017/2925* (2013.01); *A61B 2017/2933* (2013.01)

(58) Field of Classification Search
CPC .... A61B 2017/2925; A61B 2017/2933; A61B 17/1796
See application file for complete search history.

(56) References Cited

U.S. PATENT DOCUMENTS

| | | | |
|---|---|---|---|
| 5,322,055 A | 6/1994 | Davison et al. | |
| 5,814,072 A * | 9/1998 | Bonutti | A61B 17/0401 606/104 |
| 5,814,073 A * | 9/1998 | Bonutti | A61B 17/0401 604/14 |
| 5,895,395 A * | 4/1999 | Yeung | A61B 17/0469 606/139 |
| 6,533,795 B1 | 3/2003 | Tran et al. | |
| 7,104,999 B2 | 9/2006 | Overaker | |
| 7,354,442 B2 | 4/2008 | Sasso et al. | |
| 8,231,654 B2 | 7/2012 | Kaiser et al. | |
| 8,292,262 B2 | 10/2012 | Hasunuma et al. | |
| 9,717,491 B2 | 8/2017 | Hoeppner et al. | |
| 2001/0007057 A1 | 7/2001 | Lippitt et al. | |
| 2001/0044635 A1 | 11/2001 | Niizeki et al. | |
| 2006/0271074 A1 | 11/2006 | Ewers et al. | |
| 2007/0005067 A1* | 1/2007 | Dross | A61B 17/0483 606/232 |
| 2011/0009867 A1* | 1/2011 | Oren | A61B 17/0485 606/80 |
| 2012/0116450 A1* | 5/2012 | McDevitt | A61B 17/0401 606/232 |
| 2014/0107657 A1* | 4/2014 | Norton | A61B 17/1796 606/96 |
| 2014/0114330 A1* | 4/2014 | Karasic | A61B 17/1633 606/144 |
| 2014/0257314 A1* | 9/2014 | Brown | A61B 17/0401 606/98 |
| 2015/0250469 A1 | 9/2015 | Hoeppner | |

FOREIGN PATENT DOCUMENTS

| | | |
|---|---|---|
| WO | WO-0154586 A1 | 8/2001 |
| WO | WO-0167962 A2 | 9/2001 |
| WO | WO-0211630 A1 | 2/2002 |
| WO | WO-0221998 A2 | 3/2002 |
| WO | WO-03065904 A1 | 8/2003 |
| WO | WO-2004062506 A1 | 7/2004 |
| WO | WO-2005112786 A2 | 12/2005 |
| WO | WO-2005112788 A2 | 12/2005 |
| WO | WO-2006060035 A2 | 6/2006 |
| WO | WO-2006067548 A1 | 6/2006 |
| WO | WO-2006128092 A2 | 11/2006 |
| WO | WO-2007084714 A2 | 7/2007 |

OTHER PUBLICATIONS

"U.S. Appl. No. 14/202,628, Advisory Action dated Feb. 3, 2017", 3 pgs.
"U.S. Appl. No. 14/202,628, Final Office Action dated Nov. 1, 2016", 12 pgs.
"U.S. Appl. No. 14/202,628, Non Final Office Action dated Mar. 24, 2016", 10 pgs.
"U.S. Appl. No. 14/202,628, Notice of Allowance dated Mar. 27, 2017", 11 pgs.
"U.S. Appl. No. 14/202,628, Response filed Jul. 25, 2016 to Non Final Office Action dated Mar. 24, 2016", 9 pgs.
"U.S. Appl. No. 14/202,628, Response filed Dec. 3, 2015 to Restriction Requirement dated Oct. 6, 2015", 8 pgs.
"U.S. Appl. No. 14/202,628, Response filed Dec. 29, 2016 to Final Office Action dated Nov. 1, 2016", 11 pgs.
"U.S. Appl. No, 14/202,628, Restriction Requirement dated Oct. 6, 2015", 9 pgs.

* cited by examiner

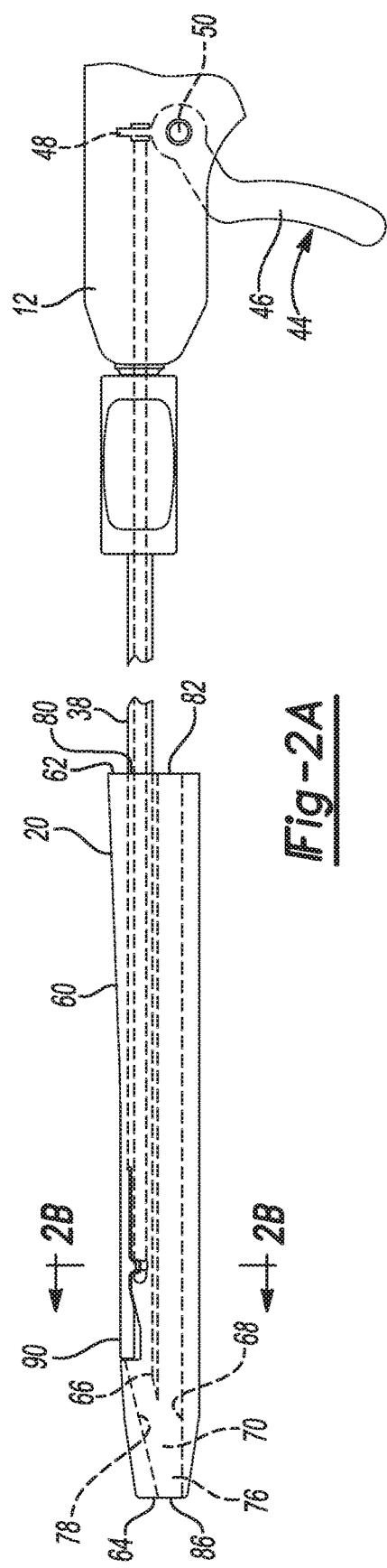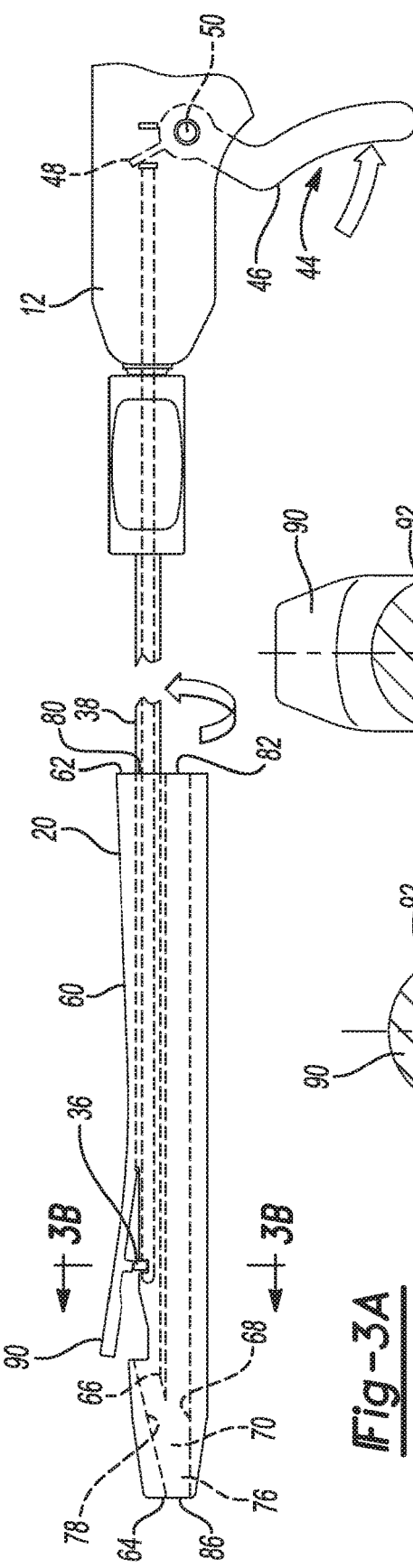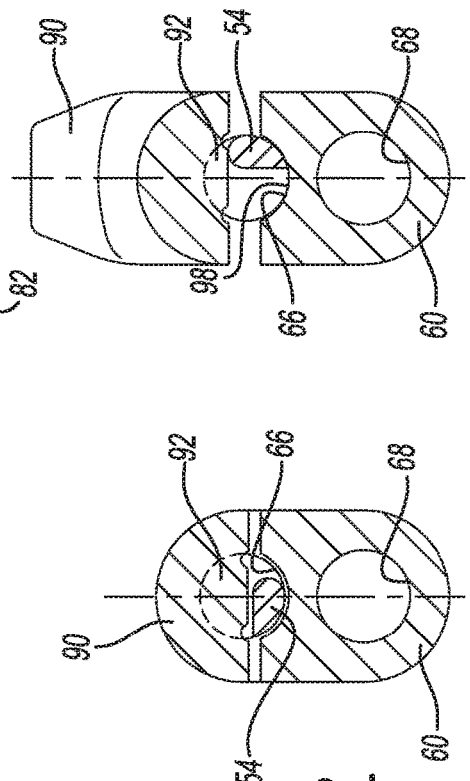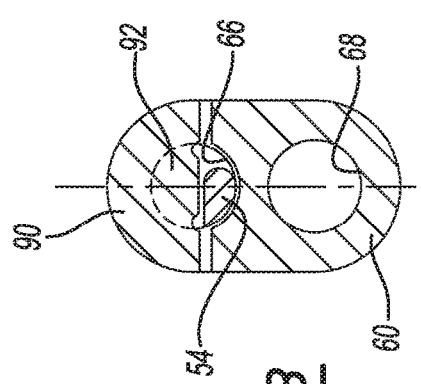

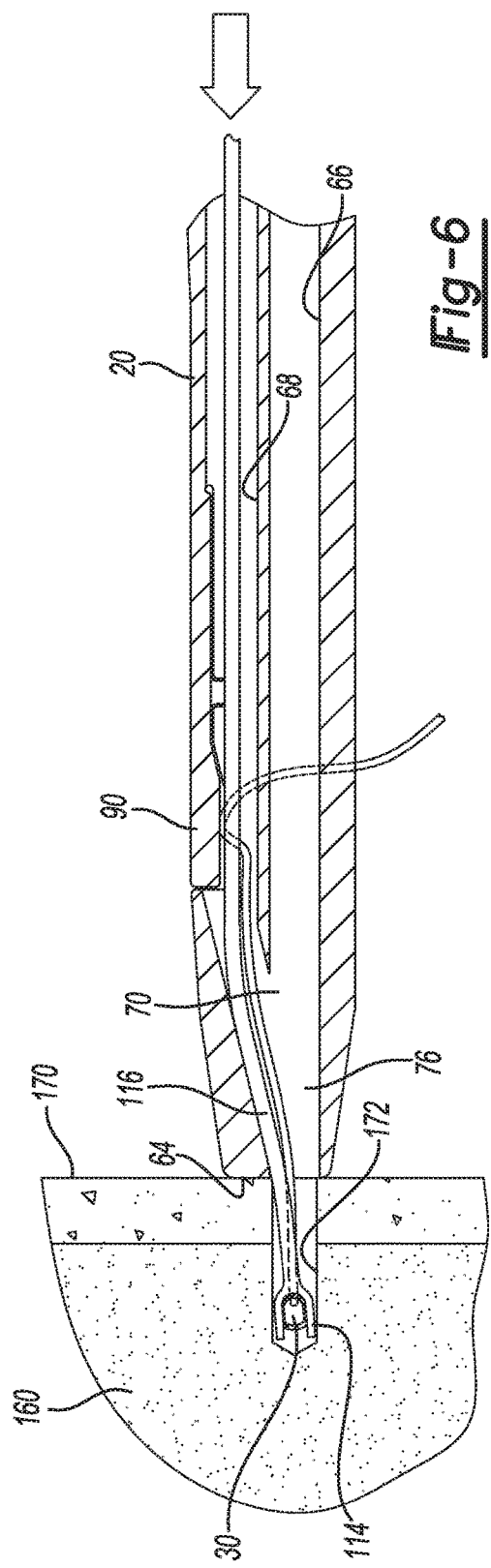
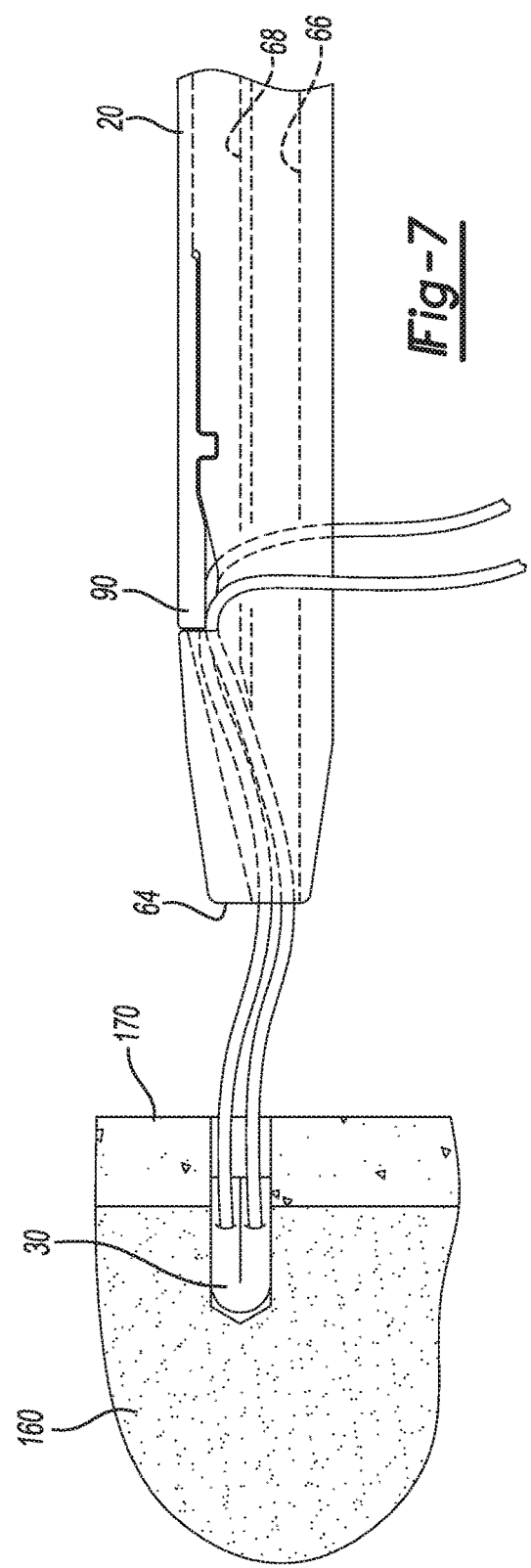

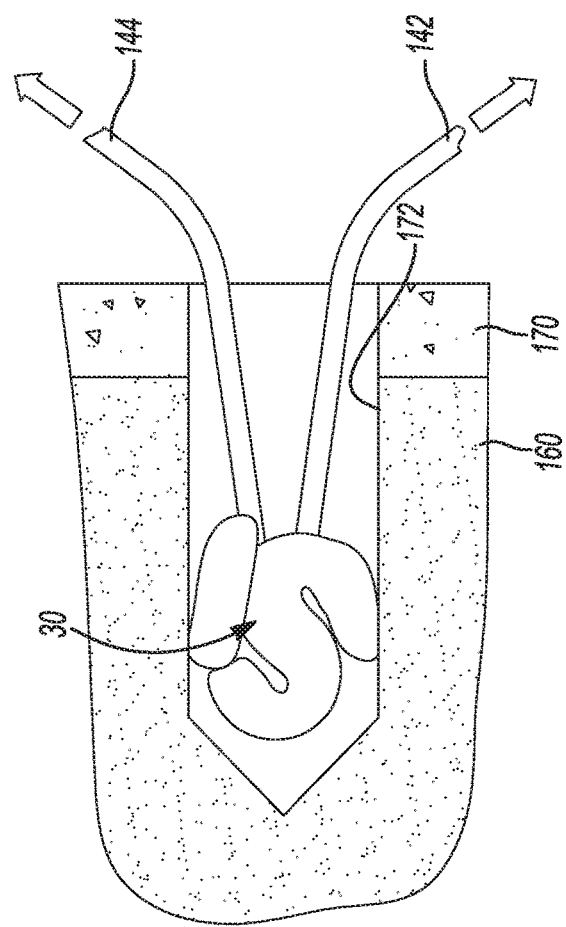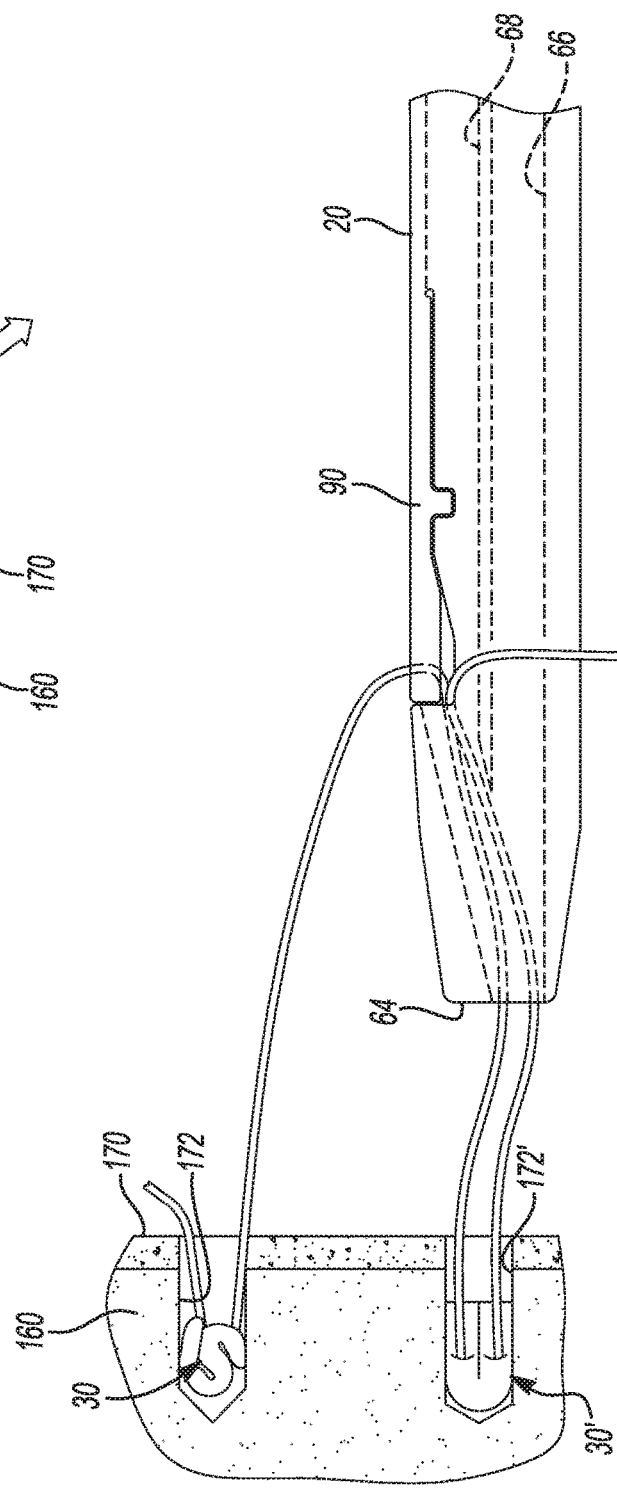

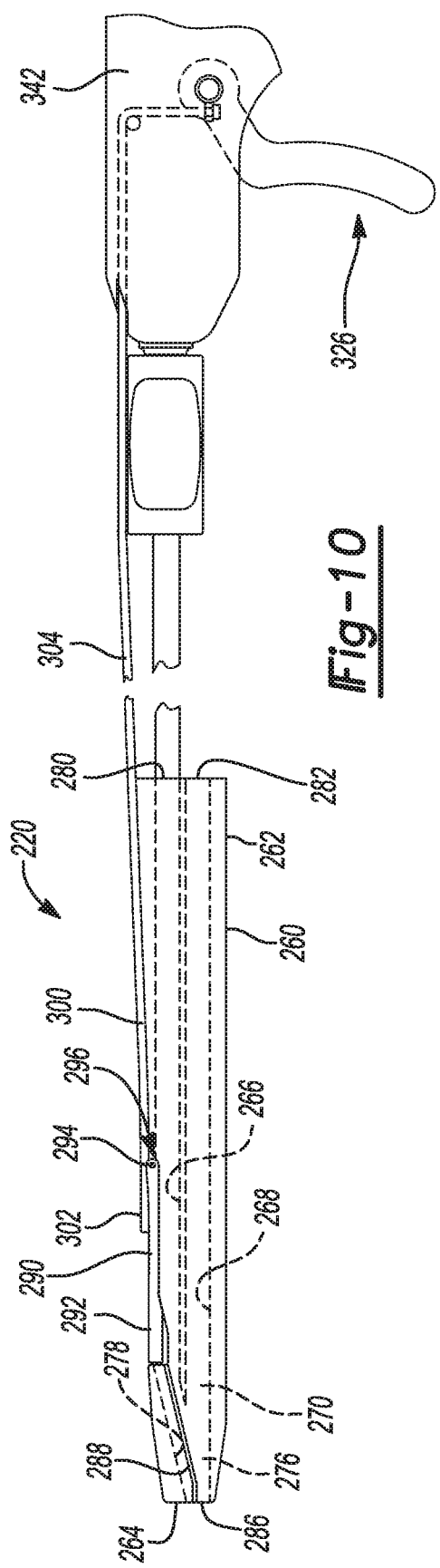
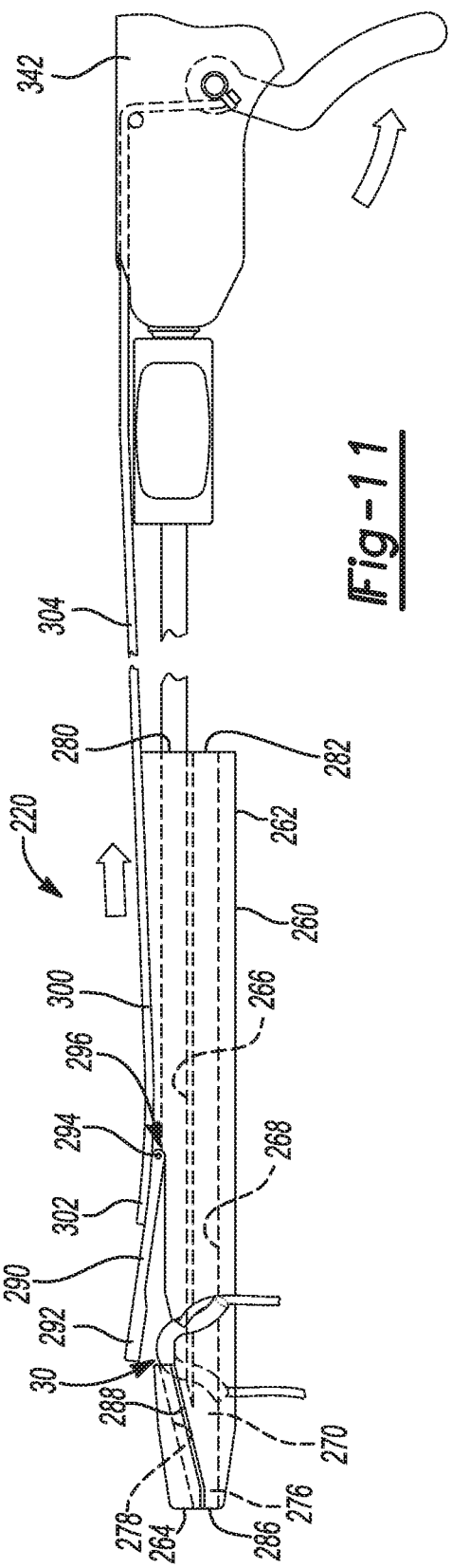

METHOD AND APPARATUS FOR COUPLING SOFT TISSUE TO BONE

FIELD

The present disclosure relates generally to a method and apparatus for coupling a suture and/or soft tissue to bone.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Surgical or medical procedures are often performed on a body, for example, a human body or anatomy, to repair or replace various portions thereof. For example, the soft tissues of the body may need to be reattached to bones due to trauma, overuse, surgical intervention, or disease. Soft tissue can be reattached to bone using devices such as screws, staples, and various types of suture anchors. One means to fix the soft tissue to the selected area is to provide a suture through a selected portion of the soft tissue and fix the other end of the suture to a selected area on the bone using a suture anchor and a pre-formed hole in the bone, which can require various different instruments and tying a knot to secure the suture to the anchor. Accordingly, there is a need for improvement in the relevant art.

SUMMARY

This section provides a general summary of the disclosure, and is not a comprehensive disclosure of its full scope or all of its features.

A flexible member securing assembly for use in securing a flexible member relative to bone can include an actuating tool and a positioning tool. The actuating tool can have an elongated member that extends between a proximal user engaging end and a distal actuating end. The proximal user engaging end can have a user actuating portion. The distal actuating end can have an actuating member. The positioning tool can have a body that extends between a proximal receiving end and a distal positioning end. The body can further comprise a first proximal opening and a grasping member movably coupled to the body between an open grasping position and a closed securing position. Movement of the actuating member can urge the grasping member toward the open grasping position.

According to additional features, the positioning tool can further define a first cannulation and a distinct second cannulation. The positioning tool can further define a converging cannulation portion proximate the distal positioning end. The first and second cannulations can converge at the converging cannulation portion into a common cannulation portion at the distal positioning end. The body can comprise a ramp formed at the converging cannulation portion. The body can further comprise a second proximal opening and a common distal opening. The body can define a slot that connects the common distal opening and the first cannulation. The first and second cannulations can be parallel and offset. The grasping member can be hingedly coupled to the body. The grasping member can be biased toward the closed securing position. The flexible member securing assembly can further include a flexible member advancing tool that is configured to be slidably received in the first proximal opening. The flexible member advancing tool can be configured to be advanced to a first position that engages the flexible member adjacent the grasping member to a second position that advances the flexible member through the distal opening. The first proximal opening can be configured to receive the distal actuating end of the actuating tool and at least a portion of the elongated member. Movement of the user actuating portion can urge the actuating member to ride on a surface of the body and urge a tang on the grasping member away from the first cannulation.

A method of securing a suture to bone according to one example of the present disclosure can include grasping a first suture portion with a grasping member on a positioning tool. The first suture portion can be located into a first cannulation defined in the positioning tool. A cutting member can be advanced through a second cannulation defined on the positioning tool and out through a distal opening defined on the positioning tool. A first bone hole can be cut into the bone with the cutting member. A flexible member advancing tool can be advanced through the first cannulation. The first suture portion can be urged out of the distal opening and into the first bone hole.

According to additional features, subsequent to urging the first suture portion into the first bone hole, a second suture portion can be grasped with the grasping member. The second suture portion can be located a distance along the suture from the first suture portion. The cutting member can be advanced through the second cannulation and out through the distal opening of the positioning tool. A second bone hole can be cut into the bone with the cutting member. The flexible member advancing tool can be advanced through the first cannulation. The second suture portion can be urged out of the distal opening and into the second bone hole.

In other features, grasping the first suture portion can include rotating an arm pivotally coupled to the positioning tool. Rotating the arm can include advancing a user actuating portion on an actuating tool causing an actuating member on the actuating tool to urge the arm to rotate from a closed securing position to an open grasping position. Advancing the flexible member advancing tool can include urging the first suture portion from the first cannulation to a converging cannulation where the first and second cannulations converge out of the distal opening. Grasping the first suture portion can include moving a user actuating portion on an actuating tool causing an actuating member to ride on a surface of the positioning tool and urge a tang on the grasping member away from the first cannulation.

A method of securing a suture to bone according to another example of the present disclosure can include actuating an arm movably coupled to a positioning tool from a normally closed position to an open grasping position. A first suture portion can be grasped with the grasping member. The first suture portion can be located relative to a first cannulation defined on the positioning tool. The positioning tool can be located at a first position against a bone surface. A cutting member can be advanced through a second cannulation defined on the positioning tool and out through a distal opening defined on the positioning tool. A first bone hole can be cut into the bone with the cutting member. With the positioning tool at the first position, a flexible member advancing tool can be advanced through the first cannulation. The first suture portion can be urged out of the distal opening and into the first bone hole.

In other features, a second suture portion can be grasped with the arm. The second suture portion can be located a distance from the first suture portion and with the positioning tool at least partially located within tissue. The positioning tool can be located at a second location against the bone, distinct from the first location. The cutting member can be advanced through a second cannulation defined on the positioning tool and out through a distal opening defined on the positioning tool. A second bone hole can be cut into the bone with the cutting member. With the positioning tool at the second position, the flexible member advancing tool can be advanced through the first cannulation. The second suture portion can be urged out of the distal opening and into the second bone hole.

According to additional features, grasping the first suture portion can include rotating the arm about a pivot pin configured on a body of the positioning tool. Rotating the arm can further include advancing a user actuating portion on an actuating tool causing an actuating member on the actuating tool to urge the arm to rotate from a closed securing position to an open grasping position. Advancing the flexible member advancing tool can further include urging the first suture portion from the first cannulation to a converging cannulation portion where the first and second cannulations converge and out of the distal opening. Urging the first suture portion with the flexible member advancing tool can include locating a distal fork of the flexible member advancing tool around the first suture portion. Subsequent to urging the first suture portion into the first bone hole, tension can be applied to the first suture portion causing a tubular sleeve on the first suture portion to change configuration from a flaccid configuration to a bunched-up configuration that provides a retaining force for the first suture portion in the first bone hole. Subsequent to urging the first suture portion into the first bone hole, the positioning tool can be moved away from the first position while passing a section of the suture through a slot defined on the positioning tool.

Further areas of applicability of the present disclosure will become apparent from the description provided hereinafter. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only and are not intended to limit the scope of the present disclosure.

FIG. 2A is a side view of an actuating tool and positioning tool of the flexible member securing assembly of FIG. 1, the positioning tool shown in a closed securing position;

FIG. 2B is a sectional view of the actuating tool and positioning tool taken along lines 2B-2B of FIG. 2A;

FIG. 3A is a side view of the actuating tool and positioning tool of FIG. 2A and shown with the positioning tool in an open grasping position;

FIG. 3B is a sectional view of the actuating tool and positioning tool taken along lines 3B-3B of FIG. 3A;

FIG. 6 is a sectional view of the positioning tool shown with a flexible member advancing tool located through the first cannulation and advancing the first connecting device to the first bone hole;

FIG. 7 is a side view of the positioning tool pulled away from the bone subsequent to placement of the first connecting device into the first bone hole;

FIG. 8 is a sectional view of the first bone hole shown subsequent to the ends of a strand on the first connecting device being pulled causing a tubular sleeve of the first connecting device to bunch up and fix the first connecting device at the first bone hole;

FIG. 9 is a sectional view of the bone shown subsequent to a second connecting device being deployed into a second bone hole;

FIG. 10 is a side view of an actuating tool and positioning tool constructed in accordance to additional features, the positioning tool shown in a closed securing position; and FIG. 11 is a side view of the actuating tool and positioning tool of FIG. 10 and shown with the positioning tool in an open grasping position;

DETAILED DESCRIPTION

The following description is merely exemplary in nature and is not intended to limit the present disclosure, its application, or uses. Although the following description is related generally to methods and apparatus for securing a flexible member to bone, it should be appreciated that the methods and apparatus discussed herein can be applicable to various bones and/or joints of the anatomy and can be utilized with various flexible members and rigid bodies or anchors. In this regard, the present teachings can be used for various orthopedic applications including coupling bone to bone, bone to soft tissue, soft tissue repair, and generally attaching soft tissue to bone, or attaching suture or other anchors to bone, or any other tissue repair procedure. The present teachings can also be used for repairing any fibrous tissue, such as muscle, ligament or tendon in an arthroscopic or other open procedure, including rotator cuff reconstruction, acromioclavicular (AC) reconstruction, anterior cruciate ligament reconstruction (ACL) and generally for fastening tendons, grafts, or strands to fibrous tissue and bone. Additionally, the present teachings can be used for repairing tissue in cardiological, laparoscopic, urological, plastic, blood vessels, annulus of spin or other procedures.

Exemplary embodiments are provided so that this disclosure will be thorough, and will fully convey the scope to those who are skilled in the art. Numerous specific details are set forth such as examples of specific components, devices, systems and/or methods, to provide a thorough understanding of exemplary embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

The present teachings provide a flexible member securing assembly and a method for using the same to secure a flexible member to bone. In an exemplary aspect, the flexible member can be a suture. The flexible member securing assembly can be provided as a kit and can include an actuating tool, a positioning tool and a flexible member advancing tool. As will become appreciated herein, the flexible member securing assembly provides a surgeon a robust and convenient set of tools that allow the surgeon to grasp and manipulate a suture within the tissue of a patient. The particular examples discussed herein relate to grasping and locating a connector device in the form of a JuggerKnot™ soft tissue anchor, marketed by Biomet Manufacturing, LLC of Warsaw, Ind. It will be appreciated, however, that the flexible member securing assembly disclosed herein may be used to grasp and manipulate other connecting devices, flexible members, sutures and the like.

Figure 1:
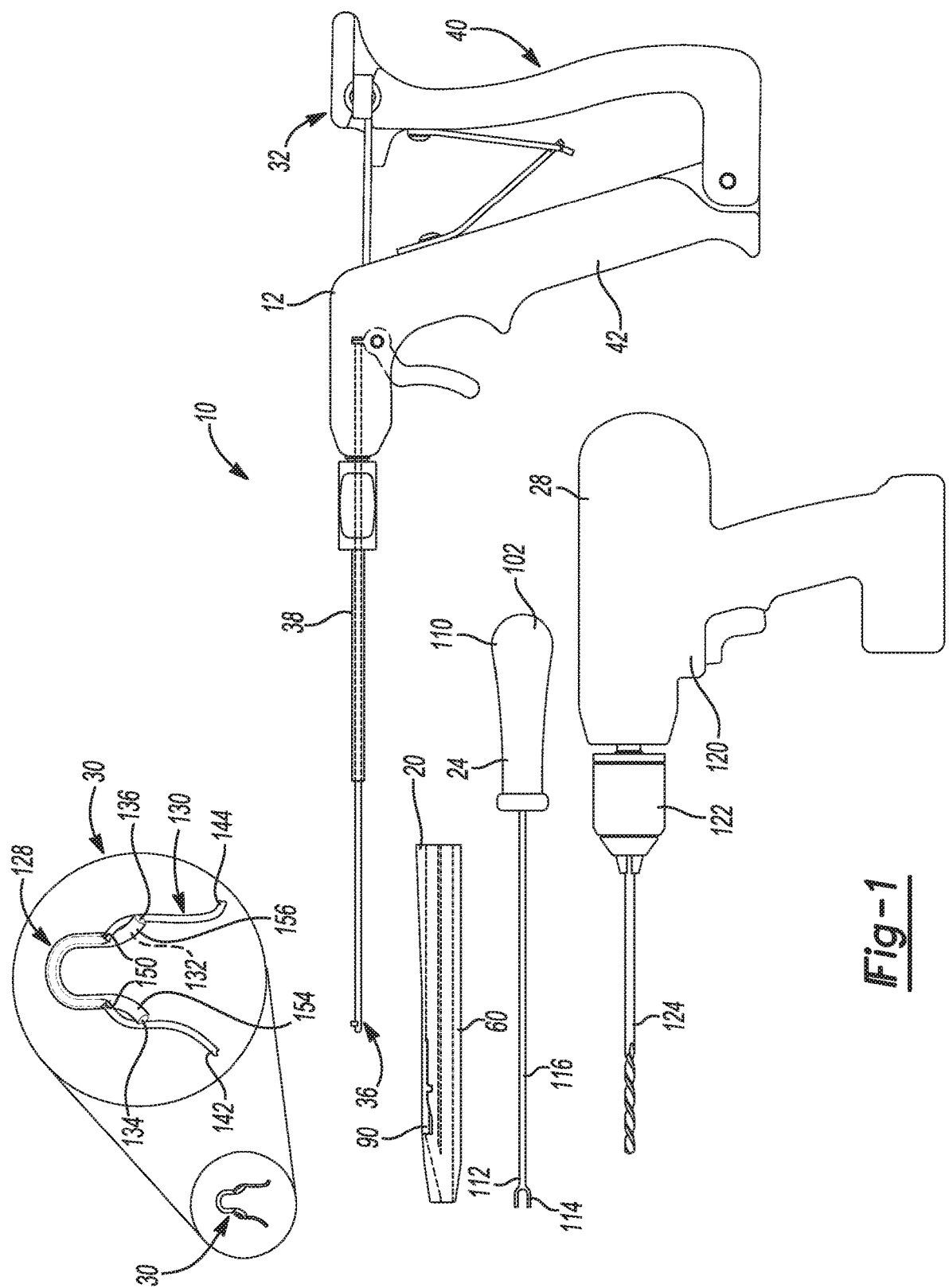
FIG. 1 is a side view of a flexible member securing assembly constructed in accordance to one example of the present disclosure.

With initial reference to FIG. 1, a flexible member securing assembly constructed in accordance to one example of the present disclosure is shown and generally identified at reference numeral 10. The flexible member securing assembly 10 can generally include an actuating tool 12, a positioning tool 20, a flexible member advancing tool 24, a drill driver 28 and a flexible member or connector device 30. Some or all of the identified components of the securing assembly 10 may be provided as a kit. For example, the actuating tool 12, the positioning tool 20 and the flexible member advancing tool 24 may be provided as a collection of tools in a kit. It is further contemplated that the kit may further include one or more flexible members 30. Other combinations are contemplated. In other examples, the components of the flexible member advancing tool 24 may be provided individually and be used in combination with other instruments.

With continued reference to FIG. 1 and additional reference to FIGS. 2A-3B the actuating tool 12 will be described in greater detail. The actuating tool 12 can generally include a proximal user engaging end 32, a distal actuating end 36 and a shaft 38. The proximal user engaging end 32 can include a gripping portion 40 having an actuating tool handle 42 and a trigger 44. The trigger 44 includes a user actuating portion 46 and a shaft engaging portion 48. In the particular example shown, the user actuating portion 46 is configured to rotate counterclockwise as shown in the figures about a pivot pin 50 from an unactuated position (FIG. 2A) to an actuated position (FIG. 3A). As will become appreciated from the following discussion, movement of the user actuating portion 46 will result in corresponding rotational movement of the shaft 38. The distal actuating end 36 of the actuating tool 12 can include an actuating member or cam 54.

With continued reference to FIGS. 1-3B, the positioning tool 20 will be further described. The positioning tool 20 can include a body 60 that extends between a proximal receiving end 62 and a distal positioning end 64. The body 60 can be a dual-cannulated body that defines a first cannulation 66 and a second cannulation 68. In the example shown, the first and second cannulations 66 and 68 are distinct passages that are parallel and offset relative to each other. The body 60 can further include a converging cannulation portion 70 proximate the distal positioning end 64. The first and second cannulations 66 and 68 can converge at the converging cannulation portion 70 into a common cannulation portion 76 at the distal positioning end 64. A ramp 78 can be provided on the body 60 at the converging cannulation portion 70. The body 60 can further define a first proximal opening 80 that leads to the first cannulation 66 and a second proximal opening 82 that leads to the second cannulation 68. The distal end 64 can define a distal opening 86.

The positioning tool 20 can include a grasping member 90. The grasping member 90 shown in FIGS. 2A-9 is an integrally formed portion of the body 60. As will be described herein however, the grasping member 90 can take other forms such as a hinged member that rotates relative to the body. The grasping member 90 can include a tang 92 formed thereon. The tang 92 can align for contact with the cam member 54 (FIGS. 2B and 3B). In the example shown in FIGS. 2A-3B, the distal actuating end 36 of the actuating tool 12 can be received by the first cannulation 66 of the positioning tool 20. Actuation of the user actuating portion 46 causes rotation of the shaft 38 around its axis. Rotation of the shaft 38 can cause the cam member 54 to ride along a track 98 formed by the body 60 at the first cannulation 66 from a first position (FIG. 2B) to a second position (FIG. 3B). As the cam member 54 rides along the track 98 it engages the tang 92 and urges the tang 92, and therefore the grasping member 90, upward as viewed from FIG. 2B to FIG. 3B. As referred to herein, the grasping member 90 therefore can move from a closed securing position (FIGS. 2A and 2B) to an open grasping position (FIGS. 3A and 3B). In the example provided, the grasping member 90 is normally in the closed securing position and can be actuated to the open grasping position. The grasping member 90 can be biased to the closed securing position.

The flexible member advancing tool 24 can generally include a first end 102 having a handle 110 and a second end 112 having a prong or fork 114. An advancing tool shaft 116 can connect the handle 110 and the fork 114. The drill driver 28 can generally include a drill actuating portion 120, a chuck portion 122 and a drill bit 124. The drill driver 28 is merely exemplary and can comprise any driver configured to provide rotational input onto the drill bit 124.

Returning to FIG. 1, the connector device 30 will be described. The connector device 30 can be used for attaching soft tissue to bone. The connector device 30 includes a flexible tubular sleeve or tube 128 and an elongated flexible member or strand 130. The tube 128 can define an inner bore 132 that extends between first and second open ends 134 and 136. The elongated flexible strand 130 can have a first end 142 and a second end 144. The flexible strand 130 can pass axially through the inner bore 132 of the sleeve 128 such that the first and second ends 142 and 144 exit the corresponding first and second open ends 134 and 136 of the flexible sleeve 128. In one configuration, the flexible member 130 can exit the bore 132 through at least one opening 150 of the flexible sleeve 128 intermediate the first and second ends 134 and 136 of the flexible sleeve 128. In the example shown, the flexible member 130 can exit the bore 132 through two openings 150 of the flexible sleeve 128 intermediate the first and second ends 134 and 136 of the flexible sleeve 128. First and second end portions or sleeve legs 154 and 156 can be provided between each end 134, 136 and the corresponding opening 150.

With reference now to FIGS. 4-9, an exemplary method of using the flexible member securing assembly 10 to secure the connector device 30 to a bone 160 will be described. As will become appreciated herein, the flexible member securing assembly 10 can be particularly useful for grasping a connector device 30 adjacent to the bone 160. In this regard, a flexible member can be engaged at multiple sequential locations (such as at multiple connector devices) along the flexible member while keeping the positioning tool 20 within a joint space. Explained further, a surgeon need not remove the positioning tool 20 entirely from a joint space subsequent placement of a first portion or first connector device of a flexible member (in this example a first JuggerKnot™) to grasp a second portion or second connector device of the flexible member (or a second JuggerKnot™). The positioning tool 20 and more generally the flexible member securing assembly 10 provides a surgeon a convenient tool system to successfully and sequentially engage multiple JuggerKnot™ portions along a flexible member to position them into successive bone holes.

Figure 4:
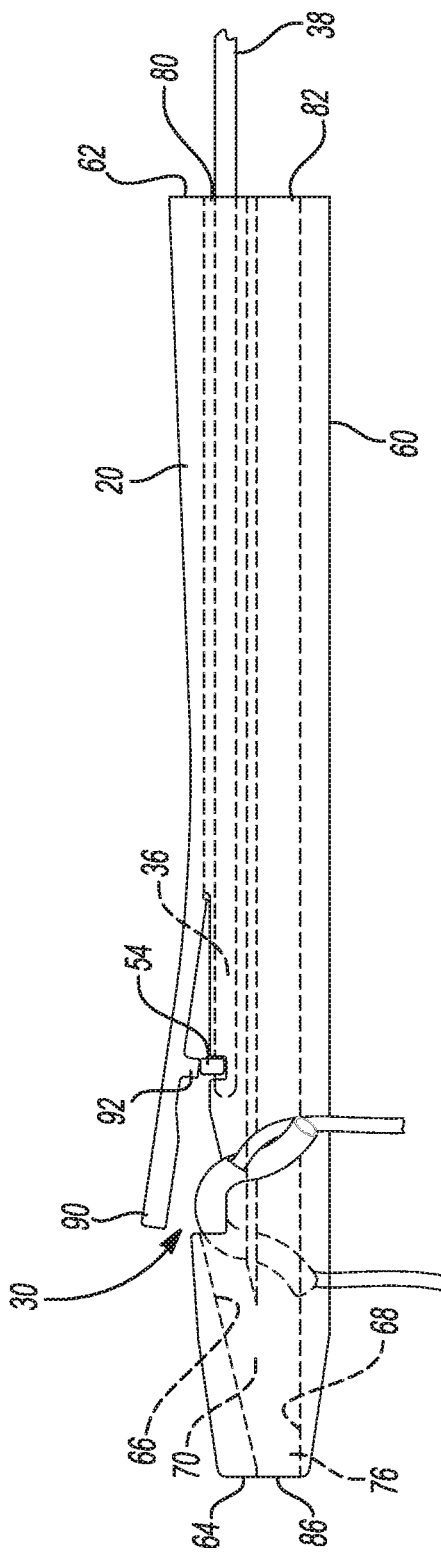
FIG. 4 is a side view of the positioning tool shown in the open grasping position and locating a first connecting device.
Figure 5:
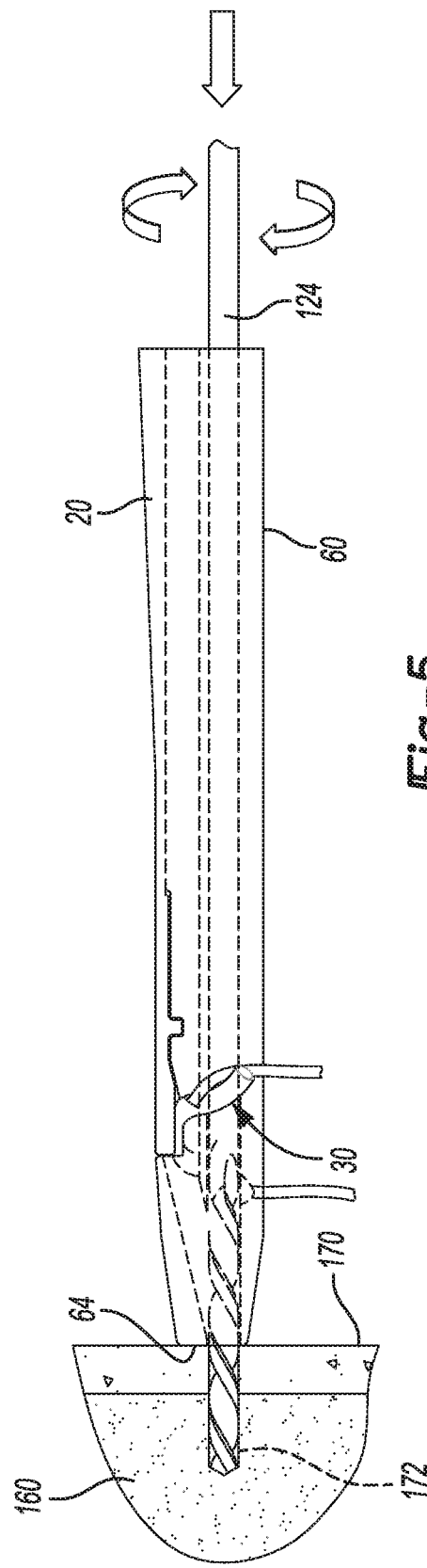
FIG. 5 is a side view of the positioning tool shown in the closed securing position with the first connecting device positioned in a first cannulation of the positioning tool and with a drill bit located through a second cannulation of the positioning tool preparing a first bone hole in a bone.

At the outset, a surgeon can locate a first suture portion or connector device 30 at the first cannulation 66 as shown in FIG. 4. In one example, the distal actuating end 36 of the actuating tool 12 can be advanced into the first cannulation 66 of the positioning tool 20. The user actuating portion 46 (FIG. 3A) can be rotated about the pivot pin 50 causing the cam member 54 to engage the tang 92 and deflect the grasping member 90 to the open grasping position. The distal positioning end 64 of the positioning tool 20 can then be located against an outer surface 170 of the bone as shown in FIG. 5. The drill bit 124 can be inserted into the second proximal opening 82 of the positioning tool 20 through the second cannulation 68, out the distal opening 86 and into the bone 160 creating a first bone hole 172. Notably, the drill bit 124 does not interfere with the connector device 30 as the connector device 30 is positioned in the first cannulation 66 offset and away from the second cannulation 68 that receives the drill bit 124.

Once the first bone hole 172 has been formed in the bone 160, the drill bit 124 can be withdrawn from the second cannulation 68 of the positioning tool 20. With the positioning tool 20 maintaining the same location against the bone 160, the fork 114 and a portion of the advancing tool shaft 116 is then advanced into the first opening 80 and along the first cannulation 66 as illustrated in FIG. 6. The fork 114 will catch the connector portion 30 and urge the connector portion 30 through the converging cannulation portion 70 and the common cannulation portion 76, out of the distal opening 86 of the body 60 and into the first bone hole 172. In one example, the fork 114 and/or the connecting portion 30 can ride along the ramp 78 directing the fork 114 toward the common cannulation portion 76 and out of the distal opening 86. In some configurations the advancing tool shaft 116 can be flexible.

Once the first connecting device 30 has been inserted into the first bone hole 172, the flexible member advancing tool 24 and the positioning tool 20 can moved away from the bone surface 170 as shown in FIG. 7. Turning now to FIG. 8, one or both ends 142 and 144 of the elongated flexible member 130 can be pulled causing tension on the flexible tubular sleeve 128. The tension on the flexible tubular sleeve 128 causes the flexible tubular sleeve 128 to change configuration, bunching up from a folded and/or flaccid configuration to a bunched-up, ball-like configuration that is retained in the first bone hole 172.

With reference now to FIG. 9, the positioning tool 20 is shown subsequent to the flexible member securing assembly 10 having prepared a second bone hole 172' in the bone 160. A second suture portion or connecting device 30' has been advanced into the second bone hole 172'. In one advantage to the flexible member securing assembly 10, the grasping member 90 can be used to grasp a second connecting device 30' proximate to an already located first connecting device 30 within the joint space and/or tissue of the patient. In this regard, multiple connecting devices 30 loaded on a flexible member 130 can be sequentially located into successive bone holes. Moreover, a surgeon need not load a successive connecting device 30 relative to a tool outside of the surgical site and pass the connecting devices 30 through cannulae.

The flexible member securing assembly 10 according to the present teachings provides an efficient apparatus and method for preparing successive bone holes and deploying corresponding connecting devices along a flexible member into the bone holes. While the first connecting member 30 has been shown already in a bunched up position, it is contemplated that in some configurations tension may be applied to the elongated flexible member 130 causing more than one connecting member 30 to change configuration from the flaccid to the bunched up position concurrently or as part of a single movement.

With reference now to FIGS. 10 and 11, a positioning tool 220 constructed in accordance to additional features will be described. The positioning tool 220 includes similar features as the positioning tool 20 described above and identified by reference numerals increased by 200. In this regard, the positioning tool 220 can include a body 260 that extends between a proximal receiving end 262 and a distal positioning end 264. The body 260 can be a dual cannulated body that defines a first cannulation 266 and a second cannulation 268. The first and second cannulations 266 and 268 can be distinct passages that are parallel and offset relative to each other. The body 260 can further include a converging cannulation portion 270 proximate to the distal positioning end 264. The first and second cannulations 266 and 268 can converge at the converging cannulation portion 270 into a common cannulation portion 276 at the distal positioning end 264. A ramp 278 can be provided on the body 260 at the converging cannulation portion 270. The body 260 can further define a first proximal opening 280 that leads to the first cannulation 266 and a second proximal opening 282 that leads to the second cannulation 268. The distal end 264 can define a distal opening 286. A slot 288 can be defined through the body 260 at the distal positioning end 264. The slot 288 can extend from the distal opening 286 to the receiving area of the connecting member 30 in the first cannulation 266. The slot 288 can allow for removal of the positioning tool 220 subsequent to placement of a connecting member 30 into the bone. In this regard, the flexible member 130 can pass through the slot 288 allowing for easy removal of the positioning tool 220 away from the bone. A similar slot may be configured on the body 60 of the positioning tool 20.

The positioning tool 220 can include a grasping member 290. The grasping member 290 can be rotatably coupled to the body 260 at a pivot pin 294. The grasping member 290, pivot pin 294 and the body 260 can collectively provide a hinge 296. An actuating member 300 can have a first end 302 that is coupled to the arm 292 and a second end 304 that is actuated by a user actuating portion 326 of an actuating tool 342. In the exemplary configuration shown, actuation of the user actuating portion 326 can cause the actuating member 300 to move rightward as viewed in FIG. 11. The first end 302 can urge the grasping member 290 to rotate about the pivot pin 294 from the position shown in FIG. 10 (closed position) to the position shown in FIG. 11 (grasping position). As with the configuration shown in FIGS. 2A and 3A, the grasping member 290 can be biased toward the closed position. It will be appreciated that the mechanical configuration for urging the grasping member 290 to rotate about the pivot pin 294 shown in the drawings is merely exemplary. For example, the arm 302 may be configured for translation within the body 260. Moreover, the mechanism shown in the actuating tool 342 may be configured differently.

Once the connector device 30 has been located at the first cannulation 266 as shown in FIG. 11, the user actuating portion 326 can be returned to the position shown in FIG. 10. The method for inserting the connector device 30 as described above may then be carried out. In this regard, one or more connector devices 30 along a flexible strand or suture 130 can then be secured into respective bone holes.

While one or more specific examples or aspects have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

The terminology used herein is for the purpose of describing particular example implementations only and is not intended to be limiting. As used herein, the singular forms "a," "an," and "the" may be intended to include the plural forms as well, unless the context clearly indicates otherwise. The term "and/or" includes any and all combinations of one or more of the associated listed items. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

What is claimed is:

1. A method of securing a suture to bone, comprising:
   grasping a first suture portion with a grasping member on a positioning tool;
   locating the first suture portion into a first cannulation defined by the positioning tool;
   advancing a cutting member through a second cannulation defined by the positioning tool, through a converging cannulation portion, and out through a distal opening defined by the positioning tool, wherein the first and second cannulations having distinct longitudinal axes, converge at the converging cannulation portion into a common cannulation portion at the distal opening of the positioning tool;
   cutting a first bone hole into the bone with the cutting member;
   advancing a flexible member advancing tool through the first cannulation and the converging cannulation portion; and
   urging the first suture portion out of the distal opening and into the first bone hole.

2. The method of claim 1, further comprising:
   subsequent to urging the first suture portion into the hole, grasping a second suture portion with the grasping member, the second suture portion located a distance along the suture from the first suture portion;
   advancing the cutting member through the second cannulation and out through the distal opening of the positioning tool;
   cutting a second bone hole into the bone with the cutting member;
   advancing the flexible member advancing tool through the first cannulation; and
   urging the second suture portion out of the distal opening and into the second bone hole.

3. The method of claim 1, wherein grasping the first suture portion comprises:
   rotating an arm pivotally coupled to the positioning tool.

4. The method of claim 3 wherein rotating the arm further comprises:
   advancing a user actuating portion on an actuating tool causing an actuating member on the actuating tool to urge the arm to rotate from a closed securing position to an open grasping position.

5. The method of claim 1, wherein the first suture portion includes a flexible tubular sleeve and an elongated strand extending through the flexible tubular sleeve.

6. The method of claim 1 wherein grasping the first suture portion comprises:
   moving a user actuating portion on an actuating tool causing an actuating member to ride on a surface of the positioning tool and urge a tang on the grasping member away from the first cannulation.

7. A method of securing a suture to bone, comprising:
   actuating an arm movably coupled to a positioning tool from a normally closed position to an open grasping position;
   grasping a first suture portion with the arm;
   locating the first suture portion relative to a first cannulation defined by the positioning tool;
   locating the positioning tool at a first position against a bone surface;
   advancing a cutting member through a second cannulation defined by the positioning tool, through a converging cannulation portion, and out through a distal opening defined by the positioning tool, while the first suture portion is grasped by the arm and located relative to the first cannulation, wherein the first and second cannulations converge at the converging cannulation portion into a common cannulation portion at the distal opening of the positioning tool;
   cutting a first bone hole into the bone with the cutting member;
   with the positioning tool at the first position, advancing a flexible member advancing tool through the first cannulation and the converging cannulation portion; and
   urging the first suture portion out of the distal opening and into the first bone hole.

8. The method of claim 7, further comprising:
   grasping a second suture portion with the arm while the positioning tool is at least partially, located within tissue, the second suture portion located a distance from the first suture portion.

9. The method of claim 8, further comprising:
   locating the positioning tool at a second position against the bone, distinct from the first position;
   advancing the cutting member through the second cannulation and out through the distal opening;
   cutting a second bone hole into the bone with the cutting member;
   with the positioning tool at the second position, advancing the flexible member advancing tool through the first cannulation; and
   urging the second suture portion out of the distal opening and into the second bone hole.

10. The method of claim 7 wherein grasping the first suture portion comprises:
    rotating the arm about a pivot pin configured on a body of the positioning tool.

11. The method of claim 10 wherein rotating the arm further comprises:
advancing a user actuating portion on an actuating tool causing an actuating member on the actuating tool to urge the arm to rotate from the closed position to the open grasping position.

12. The method of claim 7 wherein the first suture portion includes a flexible sleeve and a suture extending through the flexible sleeve.

13. The method of claim 12 wherein urging the first suture portion with the flexible member advancing tool includes locating a distal fork of the flexible member advancing tool around the first suture portion.

14. The method of claim 7, further comprising:
subsequent to urging the first suture portion into the first bone hole, applying tension to the first suture portion causing a tubular sleeve on the first suture portion to change configuration from a flaccid configuration to a bunched-up configuration that provides a retaining force for the first suture portion in the first bone hole.

15. The method of claim 7, further comprising:
subsequent to urging the first suture portion into the first bone hole, moving the positioning tool away from the first position while passing a section of the suture through a slot defined by the positioning tool.

16. A method of securing a suture to bone, comprising:
grasping a first flexible member with a grasping member on a positioning tool;
positioning the first flexible member within a first cannulation defined by the positioning tool;
advancing a cutting member through a second cannulation defined by the positioning tool and through a converging cannulation portion while the first flexible member is positioned within the first cannulation, wherein the first and second cannulations converge at the converging cannulation portion into a common cannulation portion at a distal opening of the positioning tool;
cutting a first bone hole into the bone with the cutting member;
advancing a flexible member advancing tool through the first cannulation and the converging cannulation portion; and
urging the first flexible member into the first bone hole.

17. The method of claim 16, further comprising:
coupling the first flexible member to the suture prior to urging the first flexible member into the first bone hole.

18. The method of claim 16, further comprising:
subsequent to urging the first flexible member into the hole, grasping a second flexible member with the grasping member, the second flexible member located a distance along the suture from the first suture portion;
advancing the cutting member through the second cannulation;
cutting a second bone hole into the bone with the cutting member;
advancing the flexible member advancing tool through the first cannulation; and
urging the second flexible member into the second bone hole.

19. The method of claim 16 wherein the first flexible member includes a flexible tubular sleeve, such that the suture extends through the flexible tubular sleeve.

20. The method of claim 16 wherein grasping the first flexible member comprises:
moving a user actuating portion on an actuating tool to cause an actuating member to ride on a surface of the positioning tool and urge a tang on the grasping member away from the first cannulation.

* * * * *